(12) United States Patent
Yanagi et al.

(10) Patent No.: US 7,964,735 B2
(45) Date of Patent: Jun. 21, 2011

(54) INSECTICIDAL 3-ACYLAMINOBENZANILIDES

(75) Inventors: Akihiko Yanagi, Tochigi (JP); Yukiyoshi Watanabe, Tochigi (JP); Katsuaki Wada, Tochigi (JP); Tetsuya Murata, Tochigi (JP); Jun Mihara, Tochigi (JP); Katsuhiko Shibuya, Tochigi (JP); Eiichi Shimojo, Tochigi (JP); Akira Emoto, Tochigi (JP)

(73) Assignee: Bayer Cropscience AG, Monheim (DE)

( * ) Notice: Subject to any disclaimer, the term of this patent is extended or adjusted under 35 U.S.C. 154(b) by 192 days.

(21) Appl. No.: 11/989,485

(22) PCT Filed: Jul. 21, 2006

(86) PCT No.: PCT/EP2006/007203
§ 371 (c)(1),
(2), (4) Date: Mar. 11, 2009

(87) PCT Pub. No.: WO2007/017075
PCT Pub. Date: Feb. 15, 2007

(65) Prior Publication Data
US 2009/0215623 A1    Aug. 27, 2009

(30) Foreign Application Priority Data
Jul. 29, 2005 (JP) ................................ 2005-220049

(51) Int. Cl.
| | |
|---|---|
| C07D 213/26 | (2006.01) |
| C07D 213/16 | (2006.01) |
| C07D 231/12 | (2006.01) |
| C07D 233/64 | (2006.01) |
| C07D 285/06 | (2006.01) |
| C07D 263/34 | (2006.01) |
| C07D 261/18 | (2006.01) |
| C07D 333/32 | (2006.01) |
| C07D 307/46 | (2006.01) |
| C07C 233/66 | (2006.01) |
| C07C 231/02 | (2006.01) |

(52) U.S. Cl. ........ 546/316; 546/323; 546/328; 548/127; 548/236; 548/248; 548/333.5; 548/374.1; 549/72; 549/487; 564/142; 564/155

(58) Field of Classification Search .................. None
See application file for complete search history.

(56) References Cited

U.S. PATENT DOCUMENTS
| | | |
|---|---|---|
| 2007/0027154 A1 | 2/2007 | Yoshida et al. |
| 2007/0299085 A1 | 12/2007 | Wada et al. |
| 2009/0023752 A1 | 1/2009 | Fischer et al. |

FOREIGN PATENT DOCUMENTS
| | | |
|---|---|---|
| EP | 1 380 568 A2 | 1/2004 |
| EP | 1 516 874 A1 | 3/2005 |
| GB | 1082045 | 9/1967 |
| WO | WO 2005/021488 A1 | 3/2005 |
| WO | WO 2005/073165 A1 | 8/2005 |

OTHER PUBLICATIONS

International Search Report for International Application No. PCT/EP2006/007203, European Patent Office, Netherlands, mailed on Nov. 24, 2006.

*Primary Examiner* — Brian J Davis
(74) *Attorney, Agent, or Firm* — Sterne, Kessler, Goldstein & Fox P.L.L.C.

(57) ABSTRACT

Novel 3-acylaminobenzanilides of the formula (I)

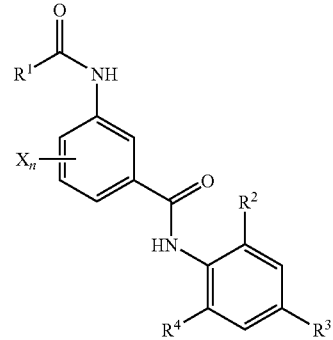

wherein $R^1$ represents phenyl which may be substituted or a 5-member or 6-member heterocyclic ring group, which may be substituted, containing at least one heteroatom selected from the group consisting of N, O, and S;
$R^2$ represents halogen, $C_{1-6}$ alkyl, or $C_{1-6}$ haloalkyl;
$R^3$ represents $C_{1-6}$ haloalkyl, $C_{1-6}$ haloalkoxy, $C_{1-6}$ haloalkylthio, $C_{1-6}$ haloalkylsulfinyl, or $C_{1-6}$ haloalkylsulfonyl;
$R^4$ represents halogen, $C_{1-6}$ alkyl, or $C_{1-6}$ haloalkyl;
X represents halogen, $C_{1-6}$ alkyl, or $C_{1-6}$ haloalkyl; and
n represents 0 or 1 and the compounds are used as insecticides, and a use of the new compounds as insecticides.

13 Claims, No Drawings

INSECTICIDAL 3-ACYLAMINOBENZANILIDES

The invention relates to new 3-acylaminobenzanilides and their utilization as insecticides.

PCT International Publication WO 2005/021488 pamphlet describes that benzamides are useful as insecticides.

There have now been found novel 3-acylaminobenzanilides of the formula (I)

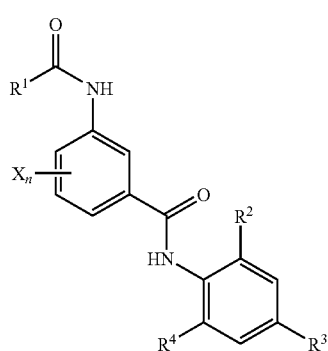

(I)

wherein $R^1$ represents phenyl which may be substituted or a 5-member or 6-member heterocyclic ring group, which may be substituted, containing at least one hetero-atom selected from the group consisting of N, O, and S;
$R^2$ represents halogen, $C_{1-6}$ alkyl, or $C_{1-6}$ haloalkyl;
$R^3$ represents $C_{1-6}$ haloalkyl, $C_{1-6}$ haloalkoxy, $C_{1-6}$ haloalkylthio, $C_{1-6}$ haloalkylsulfinyl, or $C_{1-6}$ haloalkylsulfonyl;
$R^4$ represents halogen, $C_{1-6}$ alkyl, or $C_{1-6}$ haloalkyl;
X represents halogen, $C_{1-6}$ alkyl, or $C_{1-6}$ haloalkyl; and
n represents 0 or 1.

The compound of the formula (I) of the invention can be obtained by the following production methods (a) and (b) in which Production Method (a):
compounds of the formula (II)

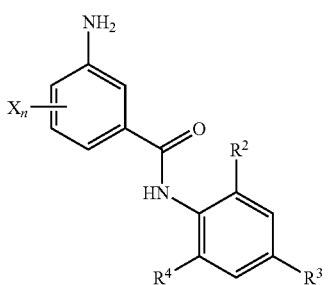

(II)

wherein $R^2$, $R^3$, $R^4$, X, and n are same as defined above, are reacted with compounds of by the formula (III)

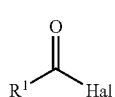

(III)

wherein $R^1$ is same as defined above and Hal represents a halogen, in the presence of inert solvents and if appropriate, in the presence of a base and a phase transfer catalyst, or Production Method (b):
compounds of the formula (IV)

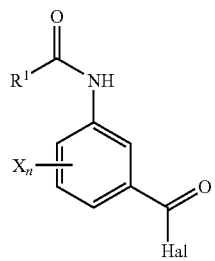

(IV)

wherein $R^1$, X, n, and Hal are same as defined above, are reacted with compounds of the formula (V)

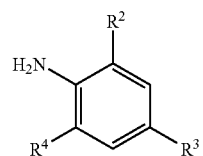

(V)

wherein $R^2$, $R^3$, and $R^4$ are same as defined, in the presence of inert solvents and if appropriate, in the presence of a base and a phase transfer catalyst.

According to the invention, 3-acylaminobenzanilides of the formula (I) as mentioned above show a powerful insecticidal effect.

The compounds of the formula (I) surprisingly shows a significantly outstanding insecticidal effect as compared with analogous compounds.

In this specification, "halogen" represents fluorine, chlorine, bromine, and iodine and preferably fluorine, chlorine, and bromine.

"Alkyl" represents, for example, a straight or branched $C_{1-12}$ alkyl such as methyl, ethyl, n- or iso-propyl, n-, iso-, sec-, or tert-butyl, n-pentyl, n-hexyl, n-heptyl, n-octyl, n-nonyl, n-decyl, n-undecyl, and n-dodecyl, preferably a $C_{1-6}$ alkyl.

The respective alkyl portions of "haloalkyl", "haloalkoxy", "haloalkylthio", "haloalkylsulfinyl", "haloalkylsulfonyl", "alkoxy", "alkylthio", "alkylsulfinyl", and "alkylsulfonyl" may be the same as described in description "alkyl".

The respective halogen portions of "haloalkyl", "haloalkoxy", "haloalkylthio", "haloalkylsulfinyl", and "haloalkylsulfonyl" may be the same as described in description "halogen".

"5-membered or 6-membered heterocyclic ring group" represents those containing at least one hetero-atom selected from a group consisting of N, O, and S and may include thienyl, furyl, pyrazolyl, imidazolyl, oxazolyl, isoxazolyl, thiadiazolyl, triazolyl, oxadiazolyl, pyridyl, pyrimidinyl, pyrazinyl, and triazinyl and particularly, thienyl, furyl, pyrazolyl, isoxazolyl, thiadiazolyl, pyridyl and pyrimidinyl.

With respect to the compounds of the formula (I) of the invention, the following compounds are preferable:
wherein $R^1$ represents a phenyl optionally substituted with at least one group selected from $C_{1-6}$ alkyl, $C_{1-6}$ alkoxy, $C_{1-6}$ alkylthio, $C_{1-6}$ alkoxysulfinyl, $C_{1-6}$ alkylsulfonyl, $C_{1-6}$ haloalkyl, $C_{1-6}$ haloalkoxy, $C_{1-6}$ haloalkylthio, $C_{1-6}$, haloalkoxysulfinyl, $C_{1-6}$ haloalkylsulfonyl, nitro, hydroxy, and halogen, or a 5-membered or 6-membered heterocyclic ring group containing at least one hetero-atom selected from the group consisting of N, O, and S and optionally substituted with at least one group selected from $C_{1-6}$ alkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkyl, $C_{1-6}$ haloalkoxy, $C_{1-6}$, haloalkylthio, $C_{1-6}$ haloalkylsulfinyl, $C_{1-6}$ haloalkylsulfonyl, nitro, hydroxy, and halogen;

$R^2$ represents halogen, $C_{1-4}$ alkyl, or $C_{1-4}$ haloalkyl;

$R^3$ represents $C_{1-4}$ haloalkyl, $C_{1-4}$ haloalkoxy, $C_{1-4}$ haloalkylthio, $C_{1-4}$ haloalkylsulfinyl, or $C_{1-4}$ haloalkylsulfonyl;

$R^4$ represents halogen, $C_{1-4}$ alkyl, or $C_{1-4}$ haloalkyl;

X represents halogen, $C_{1-4}$ alkyl, or $C_{1-4}$ haloalkyl; and n represents 0 or 1.

With respect to the compounds of the formula (I), the following compounds are particularly preferable:

wherein $R^1$ represents phenyl optionally substituted with at least one group selected from the group consisting of $C_{1-4}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ haloalkyl, $C_{1-4}$ haloalkoxy, $C_{1-4}$ haloalkylthio, $C_{1-4}$ haloalkylsulfinyl, $C_{1-4}$ haloalkylsulfonyl, nitro, hydroxy, and halogen; or pyridyl, pyrazolyl, thienyl, furyl, isoxazolyl, or thiadiazolyl optionally substituted with at least one group selected from the group consisting of $C_{1-4}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ haloalkyl, $C_{1-4}$ haloalkoxy, $C_{1-4}$ haloalkylthio, $C_{1-4}$ haloalkylsulfinyl, $C_{1-4}$ haloalkylsulfonyl, nitro, hydroxy, and halogen;

$R^2$ represents fluoro, chloro, iodo, methyl, ethyl, propyl, butyl, trifluoromethyl, or pentafluoroethyl;

$R^3$ represents $C_{1-4}$ haloalkyl, $C_{1-4}$ haloalkoxy, $C_{1-4}$ haloalkylthio, $C_{1-4}$ haloalkylsulfinyl, or $C_{1-4}$ haloalkylsulfonyl;

$R^4$ represents fluoro, chloro, iodo, methyl, ethyl, n-propyl, i-propyl, n-butyl, i-butyl, t-butyl, trifluoromethyl or pentafluoroethyl;

X represents fluoro, chloro, or methyl; and n represents 0 or 1.

Among compounds of the formula (I), the following compounds are very particularly preferable:

wherein $R^1$ represents phenyl optionally substituted with one to three groups selected from the group consisting of methyl, trifluoromethyl, fluorine, chlorine, bromine, methoxy, trifluoromethoxy, nitro and tertiary butyl; or pyridyl, pyrazolyl, thifenyl, furyl, isoxazolyl, or thiadiazolyl optionally substituted with one to three groups selected from the group consisting of methyl, trifluoromethyl, fluorine, chlorine, bromine, methoxy, trifluoromethoxy, nitro and tertiary butyl;

$R^2$ represents methyl;

$R^3$ represents perfluoroisopropyl;

$R^4$ represents iodo, methyl, ethyl or pentafluoroethyl;

X represents fluoro, chloro, or methyl; and n represents 0 or 1.

The production method (a) can be defined by the following reaction formula, for example, in the case 3-amino-N-(2,6-dimethyl-4-heptafluoroisopropylphenyl)benzamide and benzoyl chloride are used as starting raw materials.

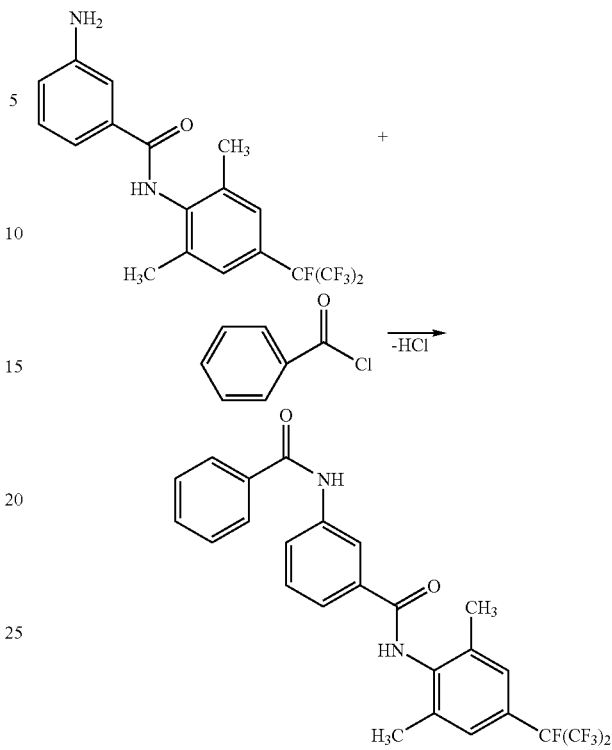

The production method (b) can be defined by the following reaction formula, for example, in the case 3-(2-chlorobenzoyl)aminobenzoic acid chloride and 2,6-dimethyl-4-heptafluoroisopropylaniline are used as starting raw materials.

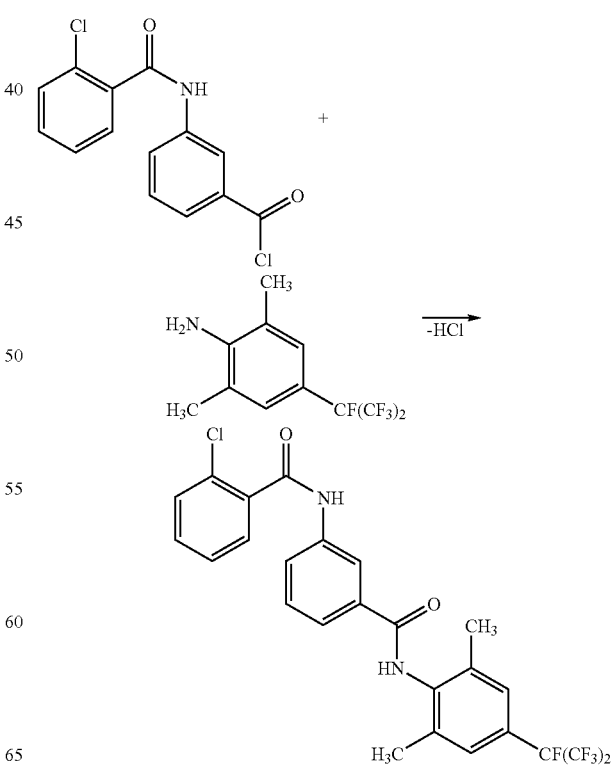

The compounds of the formula (II) to be used as a raw material in the above-mentioned production method (a) are known compounds described in WO 2005/021458 and can easily be synthesized according to the methods described in the international publication.

Representative examples of the compounds of the formula (II) include;
3-amino-N-(2,6-dimethyl-4-heptafluoroisopropylphenyl) benzamide,
3-amino-N-(2,6-dimethyl-4-heptafluoroisopropylphenyl)-2-fluorobenzamide,
3-amino-N-(2,6-dimethyl-4-heptafluoroisopropylphenyl)-2-chlorobenzamide,
3-amino-N-(2-ethyl-6-methyl-4-heptafluoroisopropylphenyl)benzamide,
3-amino-N-(2-isopropyl-6-methyl-4-heptafluoroisopropylphenyl)benzamide,
3-amino-N-(2,6-diethyl-4-heptafluoroisopropylphenyl)benzamide,
3-amino-N-(2,6-dichloro-4-heptafluoro-n-propylthiophenyl)benzamide,
3-amino-N-(2,6-dichloro-4-heptafluoro-n-propylthiophenyl)benzamide, and
3-amino-N-(2,6-dichloro-4-heptafluoro-n-propylsulfonylphenyl)benzamide.

The compounds of the formula (III) to be used as a raw material in the above-mentioned production method (a) are known compounds and many are commercialized. Or, they can easily be synthesized according to conventional methods from corresponding known carboxylic acids.

Representative examples of the compounds may include;
benzoyl chloride,
2-chlorobenzoyl chloride,
3-chlorobenzoyl chloride,
4-chlorobenzoyl chloride,
2-fluorobenzoyl chloride,
3-fluorobenzoyl chloride,
4-fluorobenzoyl chloride,
2,3-dichlorobenzoyl chloride,
2,4-dichlorobenzoyl chloride,
2,6-dichlorobenzoyl chloride,
2,3-difluorobenzoyl chloride,
2,4-difluorobenzoyl chloride,
2,6-difluorobenzoyl chloride,
nicotinyl chloride,
4-trifluoromethylnicotinyl chloride,
6-chloronicotinyl chloride,
6-fluoronicotinyl chloride,
2-fluoronicotinyl chloride,
2-chloronicotinyl chloride,
2-bromonicotinyl chloride,
2,6-difluoronicotinyl chloride,
4-chloropicolinoyl chloride,
2-chloroisonicotinyl chloride,
thiophene-3-carbonyl chloride,
2,5-dichlorothiophene-3-carbonyl chloride,
3-chlorothiophene-2-carbonyl chloride,
3-(tert-butyl)-1-methylpyrazol-5-carbonyl chloride,
4-methyl-1,2,3-thiadiazole-5-carbonyl chloride, and
4-furoyl chloride.

The reaction of the above-mentioned production method (a) can be carried out in a proper diluent. Examples of the diluent to be used in that case include aliphatic, alicyclic, and aromatic hydrocarbons (optionally chlorinated) such as pentane, hexane, cyclohexane, petroleum ether, benzene, toluene, xylene, dichloromethane, and dichloroethane; ethers such as ethyl ether, methyl ethyl ether, isopropyl ether, butyl ether, dioxane, dimethoxyethane (DME), tetrahydrofuran (THF), and diethylene glycol dimethyl ether (DGM); ketones such as acetone, methyl ethyl ketone (MEK), methyl isopropyl ketone, methyl isobutyl ketone (MIBK); nitriles such as acetonitrile, propionitrile, and acrylonitrile; esters such as ethyl acetate and amyl acetate.

The production method (a) can be carried out in the presence of a base. Such base may include as inorganic bases, hydroxides, carbonates, and dicarbonates of alkali metals such as sodium hydrogen carbonate, potassium hydrogen carbonate, sodium carbonate, potassium carbonate, lithium hydroxide, sodium hydroxide, and potassium hydroxide; as organic bases, tertiary amines, dialkylaminoanilines, and pyridines such as triethylamine, 1,1,4,4,-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), and 1,8-diazabicyclo[5,4,0]undec-7-ene (DBU).

The production method (a) can be carried out by a method using a phase transfer catalyst. Examples of the diluent to be used in that case include water; aliphatic, alicyclic, and aromatic hydrocarbons (optionally chlorinated) such as pentane, hexane, cyclohexane, benzene, toluene, xylene, ethers such as ethyl ether, methyl ethyl ether, methyl butyl ether, isopropyl ether, and butyl ether.

Examples of the phase transfer catalyst include quaternary ions such as tetramethylammonium bromide, tetrapropylammonium bromide, tetrabutylammonium bromide, tetrabutylammonium bisulfide, tetrabutylammonium iodide, trioctylmethylammonium chloride, benzyltriethylammonium bromide, butylpyridinium bromide, heptylpyridinium bromide, and benzyltriethylammonium chloride; crown ethers such as dibenzo-18-crown-6, dicyclohexyl-18-crown-6, and 18-crown-6; cryptands such as [2.2.2]-cryptate, [2.1.1]-cryptate, [2.2.1]-cryptate, [2.2.B]-cryptate, [2O2O2S]-cryptate, and [3.2.2]-cryptate.

The production method (a) can be carried out substantially in a wide temperature range. Generally, it is about −40 to about 200° C., preferably about −20 to about 150° C. Also, although the reaction is preferably carried out under normal pressure, it can be carried out under increased pressure or reduced pressure.

The aimed compounds of the formula (I) can be obtained by reacting 1 mole of the compounds of the formula (II) with 1 mole or a slight excess of the compounds of the formula (III) in a diluent for example THF in the presence of pyridine.

The compounds of the formula (IV) to be used as raw materials in the production method (b) may include known compounds and represented examples are;
3-(benzoylamino)benzoyl chloride,
3-[(2-fluorobenzoyl)amino]benzoyl chloride,
3-[(3-fluorobenzoyl)amino]benzoyl chloride,
3-[(4-fluorobenzoyl)amino]benzoyl chloride,
3-[(3-trifluoromethylbenzoyl)amino]benzoyl chloride,
3-[(2-chlorobenzoyl)amino]benzoyl chloride,
3-[(2,6-difluorobenzoyl)amino]benzoyl chloride,
3-[(4-chlorobenzoyl)amino]benzoyl chloride,
3-[(2,4-dichlorobenzoyl)amino]benzoyl chloride,
3-[(2,5-dichlorobenzoyl)amino]benzoyl chloride, and
3-(benzoylamino)-2-methylbenzoyl chloride.

The compounds of the formula (IV) can easily be obtained by halogenation of the benzoic acids corresponding to them represented by the following formula:

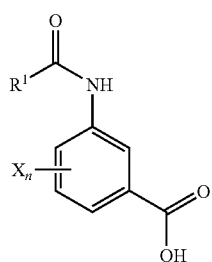

(VI)

wherein $R^1$, X, and n are same as described above.

The above-mentioned compounds of the formula (VI) can easily be obtained by hydrolyzing 3-acylaminobenoic acid esters of the following formula (VII) by conventional methods:

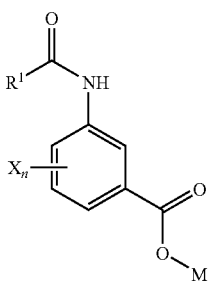

(VII)

wherein $R^1$, X, and n are same as described above and M represents $C_{1-4}$ alkyl.

The above-mentioned compounds of by the formula (VII) can easily be obtained by reaction of the compounds of the following formula:

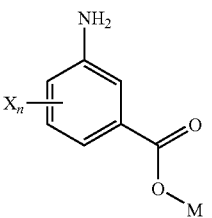

(VIII)

wherein $R^1$, X, and n are same as described above:
  with the above-mentioned compounds of the formula (III).
  The above-mentioned compounds of the formula (VIII) are well-known compounds and representative examples are;
3-aminobenzoic acid methyl ester,
3-aminobenzoic acid ethyl ester,
3-aminobenzoic acid tert-butyl ester,
3-amino-2-methylbenzoic acid ethyl ester,
3-amino-4-fluorobenzoic acid ethyl ester,
3-amino-5-fluorobenzoic acid ethyl ester, and
3-amino-2-bromobenzoic acid ethyl ester.

The compounds of the formula (V), the other raw material, in the production method (b) are well known compounds described in EP1380568 or WO 2005/021488 and can easily be produced according to the methods described in these official gazettes. Representative examples include;
2,6-dimethyl-4-pentafluoroethylaniline,
2,6-dimethyl-4-heptafluoroisopropylaniline,
2-ethyl-4-heptafluoroisopropyl-6-methyaniline,
2,6-diethyl-4-heptafluoroisopropylalinine,
2,6-dichloro-4-heptafluoroisopropylalinine,
2,6-dimethyl-4-heptafluoro-n-propylthioalinine, and
2,6-dichloro-4-heptafluoro-n-propylthioalinine.

A series of the reaction scheme relevant to the production method (b) is as follows.

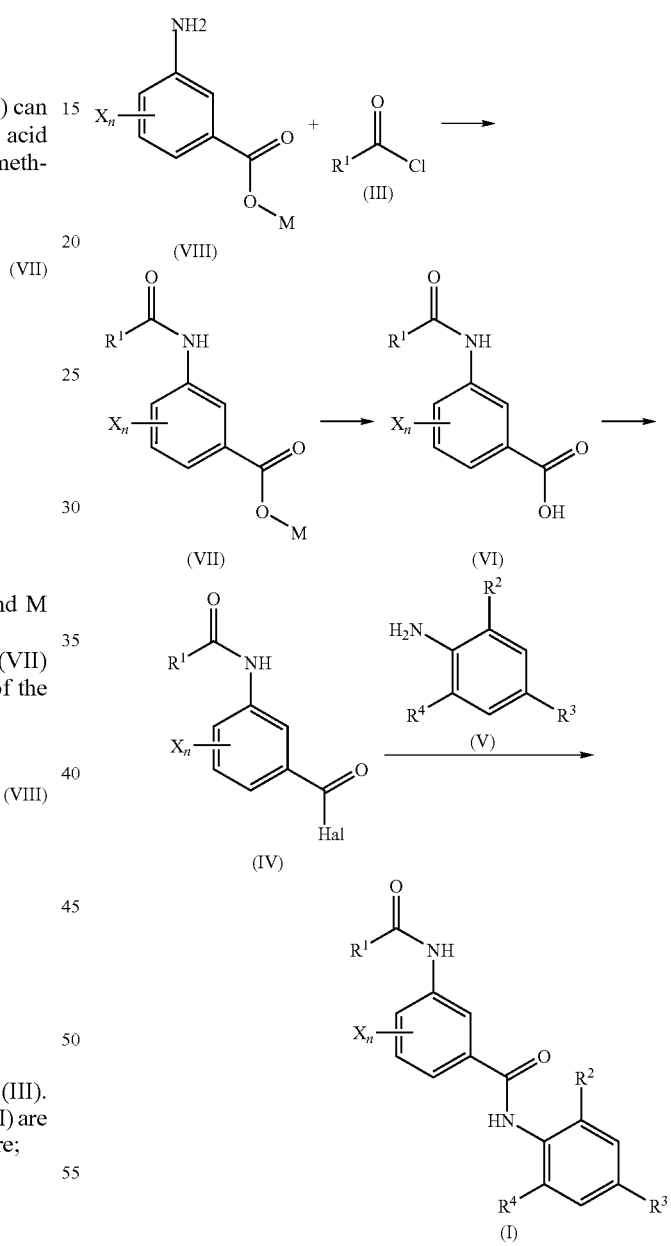

In the above shown reaction scheme, the reaction of the compound of the formula (VIII) and the compounds of the formula (III) can be carried out in a proper diluent and examples of the diluent to be used in that case include aliphatic, alicyclic, and aromatic hydrocarbons (optionally chlorinated) such as pentane, hexane, cyclohexane, petroleum ether, benzene, toluene, xylene, dichloromethane, and dichloroethane; ethers such as ethyl ether, methyl ethyl ether, isopropyl ether, butyl ether, dioxane, dimethoxyethane (DME), tetrahydrofuran (THF), and diethylene glycol dimethyl ether (DGM);

ketones such as acetone, methyl ethyl ketone (MEK), methyl isopropyl ketone, methyl isobutyl ketone (MIBK);

nitrites such as acetonitrile, propionitrile, and acrylonitrile; and esters such as ethyl acetate and amyl acetate.

The above-mentioned reaction may be carried out in the presence of a base and examples of an acid bonding agent used in the above-mentioned reaction may include as inorganic bases, hydroxides, carbonates, and dicarbonates of alkali metals such as sodium hydrogen carbonate, potassium hydrogen carbonate, sodium carbonate, potassium carbonate, lithium hydroxide, sodium hydroxide, and potassium hydroxide; as organic bases, alcolates, tertiary amines, dialkylaminoanilines, and pyridines such as triethylamine, 1,1,4,4,-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), and 1,8-diazabicyclo[5,4,0]undec-7-ene (DBU).

The above-mentioned reaction can be carried out by a method using a phase transfer catalyst. Examples of the diluent to be used in that case may includes aliphatic, alicyclic, and aromatic hydrocarbons (optionally chlorinated) such as pentane, hexane, cyclohexane, benzene, toluene, and xylene; ethers such as ethyl ether, methyl ethyl ether, methyl butyl ether, isopropyl ether, and butyl ether.

Examples of the phase transfer catalyst include quaternary ions such as tetramethylammonium bromide, tetrapropylammonium bromide, tetrabutylammonium bromide, tetrabutylammonium bisulfide, tetrabutylammonium iodide, trioctylmethylammonium chloride, benzyltriethylammonium bromide, butylpyridinium bromide, heptylpyridinium bromide, and benzyltriethylammonium chloride; crown ethers such as dibenzo-18-crown-6, dicyclohexyl-18-crown-6, and 18-crown-6; cryptands such as [2.2.2]-cryptate, [2.1.1]-cryptate, [2.2.1]-cryptate, [2.2.B]-cryptate, [2O2O2S]-cryptate, and [3.2.2]-cryptate.

The reaction can be carried out substantially in a wide temperature range. Generally, it is about –40 to about 200° C., preferably about –20 to about 110° C. Although the reaction is preferably carried out under normal pressure, it can be carried out under increased pressure or reduced pressure.

The aimed compounds of the formula (VII) can be obtained by reacting 1 mole of the compounds of the formula (VIII) with 1 mole or a slight excess of the compounds of the formula (III) in a diluent for example THF in the presence of pyridine.

The production method of the compounds of the formula (VI) by hydrolysis of the compounds of the formula (VII) can be carried out in a proper diluent and examples of the diluent are water; ethers such as ethyl ether, methyl ethyl ether, isopropyl ether, butyl ether, dioxane, and tetrahydrofuran (THF); and alcohols such as methanol, ethanol, isopropanol, butanol, and ethylene glycol.

The above-mentioned reaction is carried out using as inorganic bases, hydroxides of alkali metals and alkaline earth metals such as sodium hydroxide, potassium hydroxide, and calcium hydroxide or as inorganic acids, hydrochloric acid and sulfuric acid.

The reaction can be carried out substantially in a wide temperature range. Generally, it is about 0 to about 200° C., preferably between room temperature and about 150° C. Also, although the reaction is preferably carried out under normal pressure, it can be carried out under increased pressure or reduced pressure.

The aimed compounds of the formula (VI) can be obtained by reacting 1 mole of the compound of the formula (VII) with potassium hydroxide in a diluent, for example, a mixed solvent of water and ethanol.

The production method of the compounds of the formula (IV) from the compounds of the formula (VI) can be carried out in a proper diluent and examples of the diluent to be used in that case include aliphatic, alicyclic, and aromatic hydrocarbons (optionally chlorinated) such as hexane, cyclohexane, benzene, toluene, xylene, chlorobenzene, dichlorobenzene, dichloromethane and dichloroethane.

The above-mentioned reaction may be carried out by using as a halogenation agent, thionyl chloride and thionyl bromide and the like, and adding DMF as a catalyst.

The reaction can be carried out substantially in a wide temperature range. Generally, it is about 0 to about 200° C., preferably between room temperature to about 150° C. Also, although the reaction is preferably carried out under normal pressure, it can be carried out under increased pressure or reduced pressure.

To carry out the reaction, the aimed compounds of the formula (IV) can be obtained by adding a catalytic amount of DMF and reacting 1 mole of the compound of the formula (VI) with thionyl chloride in a diluent such as 1,2-dichloroethane.

The final reaction method (b) in the scheme can be carried out in a proper diluent and examples of the diluent to be used in that case include aliphatic, alicyclic, and aromatic hydrocarbons (optionally chlorinated) such as pentane, hexane, cyclohexane, petroleum ether, ligroin, benzene, toluene, xylene, dichloromethane, and dichloroethane;

ethers such as ethyl ether, methyl ethyl ether, isopropyl ether, butyl ether, dioxane, dimethoxyethane (DME), tetrahydrofuran (THF), and diethylene glycol dimethyl ether (DGM);

ketones such as acetone, methyl ethyl ketone (MEK), methyl isopropyl ketone, methyl isobutyl ketone (MIBK);

nitriles such as acetonitrile, propionitrile, and acrylonitrile; and esters such as ethyl acetate and amyl acetate.

The production method (b) can be carried out in the presence of a base. Examples of an acid bonding agent used in the above-mentioned reaction may include as inorganic bases, hydroxides, carbonates, and dicarbonates of alkali metals such as sodium hydrogen carbonate, potassium hydrogen carbonate, sodium carbonate, potassium carbonate, lithium hydroxide, sodium hydroxide, and potassium hydroxide; as organic bases, tertiary amines, dialkylaminoanilines, and pyridines such as triethylamine, 1,1,4,4,-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), and 1,8-diazabicyclo[5,4,0]undec-7-ene (DBU).

The production method (b) can be carried out by a method using a phase transfer catalyst. Examples of the diluent to be used in that case may be aliphatic, alicyclic, and aromatic hydrocarbons (optionally chlorinated) such as pentane, hexane, cyclohexane, benzene, toluene, and xylene; ethers such as ethyl ether, methyl ethyl ether, methyl butyl ether, isopropyl ether, and butyl ether.

Examples of the phase transfer catalyst include quaternary ions such as tetramethylammonium bromide, tetrapropylammonium bromide, tetrabutylammonium bromide, tetrabutylammonium bisulfide, tetrabutylammonium iodide, trioctylmethylammonium chloride, benzyltriethylammonium bromide, butylpyridinium bromide, heptylpyridinium bromide, and benzyltriethylammonium chloride; crown ethers such as dibenzo-18-crown-6, dicyclohexyl-18-crown-6, and 18-crown-6; cryptands such as [2.2.2]-cryptate, [2.1.1]-cryptate, [2.2.1]-cryptate, [2.2.B]-cryptate, [2O2O2S]-cryptate, and [3.2.2]-cryptate.

The production method (b) can be carried out substantially in a wide temperature range. Generally, it is about −40 to about 200° C., preferably about −20 to about 150° C. Also, although the reaction is preferably carried out under normal pressure, it can be carried out under increased pressure or reduced pressure. The aimed compounds of the formula (I) can be obtained by reacting 1 mole of the compounds of the formula (IV) with 1 mole or a slight excess of the compounds of the formula (V) in a diluent for example THF in the presence of pyridine.

The compounds of the formula (I) show a powerful insecticidal effect. Therefore, the compounds can be used as insecticides. The active compounds of the formula (I) exhibit reliable anti-insects effects to harmful insects without damaging to the grown plants. The compounds of the invention can be used for prevention of the harm of a wide range of various harmful insects, for example, harmful sucking type insects, chewing type insects, and other plant-parasitic insects, storage insects, hygienically harmful insects and prevention of breeding and extermination of them.

Such harmful insects may include the following harmful insects.

Examples of the insects may include Coleoptera such as *Callosobruchus Chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus*, and *Lyctus bruneus;*

Lipidtera such as *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotisfucosa, Galleria mellonella, Plutella maculipennis, Heliothis virescens*, and *Phyllocnistis citrella;*

Himiptea such as *Nephotettix cincticeps, Nilaparvata lugens, Pseudococcus comstocki, Unaspis yanonensis, Myzus persicas, Aphis pomi, Aphis gossypii, Phopalosiphum pseudobrassicas, Stephanitis nashi, Nazara* spp., *Trialeurodes vaporariorum*, and *Pshylla* spp.;

Thysanoptera such as *Thrips palmi*, and *Franklinella occidental;*

Orthoptera such as *Blatella germanica, Periplaneta americana, Gryllotalpa africana*, and *Locusta migratoria migratoriodes;*

Isoptera such as *Reticulitermes speratus*, and *Coptotermes formosanus;*

Diptera such as *Musca domestica, Aedes aegypti, Hylemia platura, Culex pipens, Anopheles sinensis, Culex tritaeniorhychus*, and *Liriomyza trifolii;*

Acarina such as *Tetranychus cinnabarinus, Tetranychus urticae, Panonychus citri, Aculops pelekassi*, and *Tarsonemus* spp.; and Ascaris such as *Meloidogyne incognita, Bursaphelenchus lignicolus Mamiya* et *Kiyohara, Aphelenchoides besseyi, Heterodera glycines*, and *Pratylenchus* spp.

In the veterinary field, the new compounds of the invention can effectively be used to various harmful animal parasites (internal and external parasites) for examples Insecta and Helminth.

Examples of such animal parasites may include the following harmful insects.

Examples of Insecta include *Gastrophilus* spp., *Stomoxys* spp., *Trichodectes* spp., *Rhodnius* spp., *Ctenocephalides canis*, and *Cimx lecturius.*

Examples of Acarina include *Ornithodoros* spp., *Ixodes* spp, and *Boophilus* spp.

In the invention, the substances having insecticidal effects on the harmful insects including all of the involved insects may sometimes be called insectides.

In the case the active compounds of the invention are used as insecticides, they can be formed in general formulations. The forms of the formulations are, for example, liquid agents, emulsions, hydrated agents, granular hydrated agents, suspension agents, powder agents, foaming agents, pastes, tablets, granules, aerosol, active compound dampening, natural and synthesized products, microcapsules, coated agents for seeds, formulations provided with combustion apparatus (for example, fumigation and smoking cartridges, cans, and coils as the combustion apparatus), and ULV (cold mist and warm mist).

These formulations can be produced by known methods. For example, the active compounds can be produced by developers, that is, by mixing liquid diluents or carriers; liquid gas diluents or carrier, solid diluents or carriers, and optionally, surfactants, that is, emulsifiers and/or dispersants and/or foam-forming agents with them.

In the case water is used as a developer, organic solvents, for example, may be used as auxiliary solvents.

Examples of the liquid deluents or carriers include aromatic hydrocarbons (e.g. xylene, toluene, alkylnaphthalene); chloroaromatic or chloroaliphatic hydrocarbons (e.g. chlorobenzenes, ethylene chlorides, methylene chlorides), aliphatic hydrocarbons (e.g. cyclehexane, paraffins (e.g. mineral oil fractions)), alcohols (e.g. butanol, glucol, and their ethers and esters), ketones (e.g. acetone, methyl ethyl ketone, methyl isobutyl ketone, cyclohexanone), strong-polar solvents (e.g. dimethylformamide and dimethyl sulfoxide), and water.

The liquid gas diluents or carriers are those which are gases at normal temperature and normal pressure and examples are aerosol jetting agents such as furan, propane, nitrogen gas, carbon dioxide, halohydrocarbons.

Examples of the solid diluents include milled natural minerals (e.g. kaolin, clay, talc, choke, quartz, attapulgite, montmorillonite, or kieselguhr), milled synthetic minerals (e.g. highly dispersed silicic acid, alumina, silicates).

Examples of the solid carriers for granules include crushed and classified rocks (e.g. calcite, marble, pumice, socialite, muscovite, etc.), synthesized granules of inorganic or organic powders, and fine granules of organic substances (e.g. saw dust, coconut husk, stalk of corns, and stalk of tobacco).

Examples of emulsifiers and/or foaming agents include nonionic and anionic emulsifiers (e.g. polyoxyethylene fatty acid esters, polyoxyethylene fatty acid alcohol ethers (e.g. alkyl aryl polyglycol ether), alkylsulfonic acid salts, alkylsulfuric acid salts, and arylsulfonic acid salts) and albumin hydrolysis products.

Examples of the dispersants involve lignin sulfite waste solutions, and methyl cellulose. The solid agents may be used for the formulations (powder agents, granular agents, and emulsions) and examples of the binding agents may include carboxymethyl cellulose, natural and synthetic polymers (e.g. gum arabi, poly(vinyl alcohol), and poly(vinylacetate)).

Coloring agents may be used and examples of the coloring agents include inorganic pigments (e.g. iron oxide, titanium oxide, Prussian blue); organic dyes such as Alizarine dyes, azo dyes, and metal phthalocyanine dyes; and also trace elements such as salts of iron, manganese, boron, copper, cobalt, molybdenum, and zinc.

Generally, the formulations may contain the active components in a range of 0.1 to 95% by weight, preferably 0.5 to 90% by weight.

The active compounds of the formula (I) may be in form of mixed agents with other active compounds, for example, insecticides, poisonous feeds, sterilizers, Acarina-cides, Ascaris-cides, anti-molding agents, breeding control agents, and herbicides in commercially usable formulations and application forms produced from these formulations. Herein, examples of the insecticides are organic phosphorus agents, carbamate agents, carboxylate chemical agents, chlorohydrocarbon type chemical agents, and insecticidal substance produced by microorganism.

The active compounds of the formula (I) may be in form of mixed agents with synergists and the formulations and the applications of them may be those which are commercially usable and the synergists are compounds which are not active themselves but intensify the function of the active compounds.

The contents of the active compounds of the formula (I) in commercialized application forms can be changed in a wide range.

The concentration of the practical use of the active compounds of the formula (I) may be in a range of 0.0000001 to 100% by weight, preferably 0.00001 to 1% by weight.

The compounds of the formula (I) may be used in common manners adequate to the applications.

The active compounds of the invention have efficient stability to alkali of lime substances in the case of use for hygienically harmful insects and harmful insects to storage products and have excellent sustainable property in wood and soil.

Next, the invention will be described more concretely along with Examples; however it is not intended that the invention be limited to the illustrated examples.

Synthesis Example 1

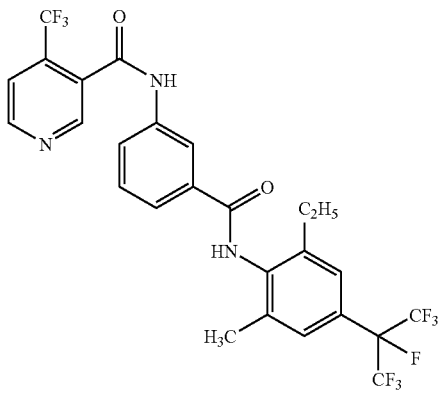

3-amino-N-(2-ethyl-6-methyl-4-heptafluoroisopropylphenyl)benzamide (0.21 g) and triethylamine (0.07 g) were added to THF (30 mL) and 4-trifluoromethylnicotinyl chloride (0.12 g) was added and stirred at room temperature for 2 hours. On completion of the reaction, the solvent was removed by distillation at a reduced pressure and the obtained residue was refined by silica gel column chromatography (n-hexane-ethyl acetate mixed solvent) to obtain an aimed product, 3-[4-(trifluoromethyl)nicotinyl]amino-N-(2-ethyl-6-methyl-4-heptafluoroisopropylphenyl)benzamide (0.26 g).

melting point: 176 to 179° C.

Synthesis Example 2

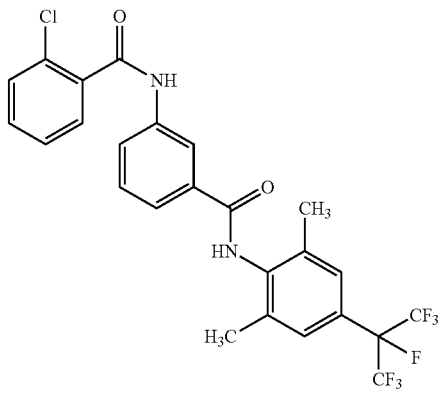

3-(2-chlorobenzoyl)aminobenzoyl chloride (0.30 g) was added to a THF solution (10 mL) of 2,6-dimethyl-4-heptafluoroisopropylaniline (0.32 g), pyridine (0.16 mL), and 4-dimethylaminopyridine (0.012 g) at a room temperature. After the reaction mixture was stirred at room temperature for 16 hours, it was poured to water and extracted with ethyl acetate. The organic layer was washed with 2N hydrochloric acid and dried with anhydrous magnesium sulfate. The solvent was removed by distillation at a reduced pressure and the obtained residue was refined by silica gel column chromatography (n-hexane-ethyl acetate mixed solvent) to obtain an aimed product, 3-(2-chlorobenzoyl)amino-N-(2,6-dimethyl-4-heptafluoroisopropylphenyl)benzamide (0.23 g).

melting point: 141 to 145° C.

The compounds defined by the formula (I) and obtained by same methods as those of the above-mentioned Synthesis Example 1 or 2 are shown in Table 1. The compounds obtained by the Synthesis Examples 1 and 2 are also shown in Table 1.

TABLE 1

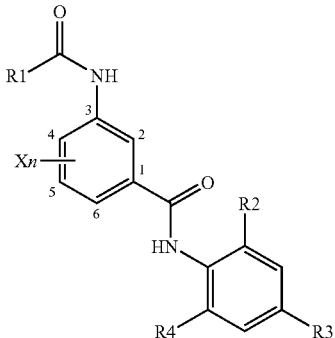

| No. | R1 | R2 | R3 | R4 | n | X | M.p. ° C. |
|---|---|---|---|---|---|---|---|
| 1 | 4-(trifluoromethyl)pyridin-3-yl | $CH_3$ | $CF(CF_3)_2$ | $C_2H_5$ | 0 | — | 176-179 |
| 2 | 4,6-difluoropyridin-3-yl | $CH_3$ | $CF(CF_3)_2$ | $C_2H_5$ | 0 | — | 181-182 |

TABLE 1-continued

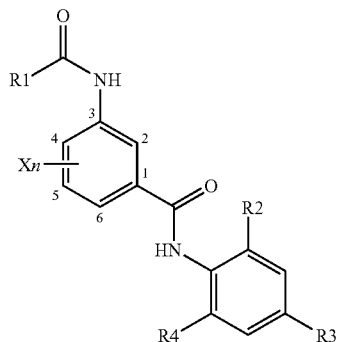

| No. | R1 | R2 | R3 | R4 | n | X | M.p. ° C. |
|---|---|---|---|---|---|---|---|
| 3 | 6-chloropyridin-3-yl | CH$_3$ | CF(CF$_3$)$_2$ | C$_2$H$_5$ | 0 | — | 237-238 |
| 4 | 6-chloropyridin-3-yl | CH$_3$ | CF(CF$_3$)$_2$ | CH$_3$ | 0 | — | |
| 5 | 2-fluoropyridin-3-yl | CH$_3$ | CF(CF$_3$)$_2$ | C$_2$H$_5$ | 0 | — | 102-105 |
| 6 | 2-chloropyridin-3-yl | CH$_3$ | CF(CF$_3$)$_2$ | C$_2$H$_5$ | 0 | — | 121-124 |
| 7 | 2-bromopyridin-3-yl | CH$_3$ | CF(CF$_3$)$_2$ | C$_2$H$_5$ | 0 | — | 118-120 |
| 8 | 5-chloropyridin-3-yl | CH$_3$ | CF(CF$_3$)$_2$ | C$_2$H$_5$ | 0 | — | |
| 9 | 2-methypyridin-3-yl | CH$_3$ | CF(CF$_3$)$_2$ | CH$_3$ | 0 | — | |
| 10 | 2-methylpyridin-3-yl | CH$_3$ | CF(CF$_3$)$_2$ | C$_2$H$_5$ | 0 | — | |
| 11 | pyridin-3-yl | CH$_3$ | CF(CF$_3$)$_2$ | CH$_3$ | 0 | — | |
| 12 | pyridin-3-yl | CH$_3$ | CF(CF$_3$)$_2$ | C$_2$H$_5$ | 0 | — | |
| 13 | 3-chloro-5-(trifluoromethyl)pyridin-2-yl | CH$_3$ | CF(CF$_3$)$_2$ | C$_2$H$_5$ | 0 | — | 203-205 |
| 14 | 3,5-dichloropyridin-2-yl | CH$_3$ | CF(CF$_3$)$_2$ | C$_2$H$_5$ | 0 | — | |
| 15 | 3-chloropyridin-2-yl | CH$_3$ | CF(CF$_3$)$_2$ | C$_2$H$_5$ | 0 | — | |
| 16 | 3-(trifluoromethyl)pyridin-2-yl | CH$_3$ | CF(CF$_3$)$_2$ | CH$_3$ | 0 | — | |
| 17 | 3-(trifluoromethyl)pyridin-2-yl | CH$_3$ | CF(CF$_3$)$_2$ | C$_2$H$_5$ | 0 | — | |
| 18 | pyridin-2-yl | CH$_3$ | CF(CF$_3$)$_2$ | CH$_3$ | 0 | — | |
| 19 | pyridin-2-yl | CH$_3$ | CF(CF$_3$)$_2$ | C$_2$H$_5$ | 0 | — | |
| 20 | 2,6-dichloropyridin-4-yl | CH$_3$ | CF(CF$_3$)$_2$ | C$_2$H$_5$ | 0 | — | |
| 21 | 2-chloropyridin-4-yl | CH$_3$ | CF(CF$_3$)$_2$ | C$_2$H$_5$ | 0 | — | |
| 22 | pyridin-4-yl | CH$_3$ | CF(CF$_3$)$_2$ | CH$_3$ | 0 | — | |
| 23 | pyridin-4-yl | CH$_3$ | CF(CF$_3$)$_2$ | C$_2$H$_5$ | 0 | — | |
| 24 | 2,5-dichlorothiophen-3-yl | CH$_3$ | CF(CF$_3$)$_2$ | C$_2$H$_5$ | 0 | — | 90-94 |
| 25 | 2-chlorothiophen-3-yl | CH$_3$ | CF(CF$_3$)$_2$ | C$_2$H$_5$ | 0 | — | |
| 26 | thiophen-3-yl | CH$_3$ | CF(CF$_3$)$_2$ | C$_2$H$_5$ | 0 | — | |
| 27 | 5-chlorothiophen-2-yl | CH$_3$ | CF(CF$_3$)$_2$ | C$_2$H$_5$ | 0 | — | |
| 28 | 3-chlorothiophen-2-yl | CH$_3$ | CF(CF$_3$)$_2$ | CH$_3$ | 0 | — | |
| 29 | 3-chlorothiophen-2-yl | CH$_3$ | CF(CF$_3$)$_2$ | C$_2$H$_5$ | 0 | — | |
| 30 | thiophen-2-yl | CH$_3$ | CF(CF$_3$)$_2$ | C$_2$H$_5$ | 0 | — | 182 |
| 31 | thiophen-2-yl | CH$_3$ | CF(CF$_3$)$_2$ | CH$_3$ | 0 | — | |
| 32 | furan-2-yl | CH$_3$ | CF(CF$_3$)$_2$ | C$_2$H$_5$ | 0 | — | 97-99 |
| 33 | furan-2-yl | CH$_3$ | CF(CF$_3$)$_2$ | CH$_3$ | 0 | — | |
| 34 | 3-(tert-butyl)-1-methylpyrazol-5-yl | CH$_3$ | CF(CF$_3$)$_2$ | C$_2$H$_5$ | 0 | — | 102-106 |
| 35 | 4-methyl-1,2,3-thiadiazol-5-yl | CH$_3$ | CF(CF$_3$)$_2$ | C$_2$H$_5$ | 0 | — | 223-224 |
| 36 | 2-iodophenyl | CH$_3$ | CF(CF$_3$)$_2$ | C$_2$H$_5$ | 0 | — | 134-141 |
| 37 | 2-chlorophenyl | CH$_3$ | CF(CF$_3$)$_2$ | I | 0 | — | 101-105 |
| 38 | 2-chlorophenyl | CH$_3$ | CF(CF$_3$)$_2$ | C$_2$H$_5$ | 0 | — | 91-96 |
| 39 | 4-(trifluoromethoxy)phenyl | CH$_3$ | CF(CF$_3$)$_2$ | C$_2$H$_5$ | 0 | — | 153-155 |
| 40 | 2-bromophenyl | CH$_3$ | CF(CF$_3$)$_2$ | C$_2$H$_5$ | 0 | — | 105-109 |
| 41 | 3-bromophenyl | CH$_3$ | CF(CF$_3$)$_2$ | C$_2$H$_5$ | 0 | — | 164-167 |
| 42 | 4-bromophenyl | CH$_3$ | CF(CF$_3$)$_2$ | C$_2$H$_5$ | 0 | — | 205-206 |
| 43 | 3,4-dichlorophenyl | CH$_3$ | CF(CF$_3$)$_2$ | C$_2$H$_5$ | 0 | — | 133-135 |
| 44 | 2,4-dichlorophenyl | CH$_3$ | CF(CF$_3$)$_2$ | C$_2$H$_5$ | 0 | — | 129-134 |
| 45 | 3,5-dichlorophenyl | CH$_3$ | CF(CF$_3$)$_2$ | C$_2$H$_5$ | 0 | — | 175-176 |
| 46 | 2,6-dichlorophenyl | CH$_3$ | CF(CF$_3$)$_2$ | C$_2$H$_5$ | 0 | — | 137-140 |
| 47 | 2,3-dichlorophenyl | CH$_3$ | CF(CF$_3$)$_2$ | C$_2$H$_5$ | 0 | — | 123-128 |
| 48 | 2,5-dichlorophenyl | CH$_3$ | CF(CF$_3$)$_2$ | C$_2$H$_5$ | 0 | — | 115-120 |
| 49 | 4-(trifluoromethyl)phenyl | CH$_3$ | CF(CF$_3$)$_2$ | C$_2$H$_5$ | 0 | — | 195-197 |
| 50 | 3-(trifluoromethyl)phenyl | CH$_3$ | CF(CF$_3$)$_2$ | C$_2$H$_5$ | 0 | — | |
| 51 | 2-(trifluoromethyl)phenyl | CH$_3$ | CF(CF$_3$)$_2$ | C$_2$H$_5$ | 0 | — | 134-139 |
| 52 | 2,4,6-trifluorophenyl | CH$_3$ | CF(CF$_3$)$_2$ | C$_2$H$_5$ | 0 | — | 223-224 |
| 53 | 2-nitrophenyl | CH$_3$ | CF(CF$_3$)$_2$ | C$_2$H$_5$ | 0 | — | 110-115 |
| 54 | 2,6-difluorophenyl | CH$_3$ | CF(CF$_3$)$_2$ | C$_2$H$_5$ | 0 | — | 118-121 |
| 55 | 2,3-difluorophenyl | CH$_3$ | CF(CF$_3$)$_2$ | C$_2$H$_5$ | 0 | — | 165-167 |
| 56 | 2,4-difluorophenyl | CH$_3$ | CF(CF$_3$)$_2$ | C$_2$H$_5$ | 0 | — | 187-188 |
| 57 | 2-chlorophenyl | CH$_3$ | CF(CF$_3$)$_2$ | C$_2$H$_5$ | 0 | — | 114-120 |
| 58 | 3-chlorophenyl | CH$_3$ | CF(CF$_3$)$_2$ | C$_2$H$_5$ | 0 | — | 162-165 |
| 59 | 4-chlorophenyl | CH$_3$ | CF(CF$_3$)$_2$ | C$_2$H$_5$ | 0 | — | 163-168 |
| 60 | 4-methoxyphenyl | CH$_3$ | CF(CF$_3$)$_2$ | C$_2$H$_5$ | 0 | — | 192-194 |
| 61 | 4-fluorophenyl | CH$_3$ | CF(CF$_3$)$_2$ | C$_2$H$_5$ | 0 | — | 174-176 |
| 62 | 3-fluorophenyl | CH$_3$ | CF(CF$_3$)$_2$ | C$_2$H$_5$ | 0 | — | 175-177 |

TABLE 1-continued

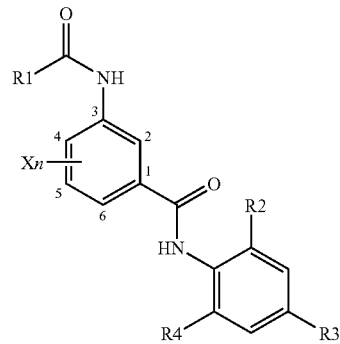

| No. | R1 | R2 | R3 | R4 | n | X | M.p. ° C. |
|---|---|---|---|---|---|---|---|
| 63 | 2-fluorophenyl | CH$_3$ | CF(CF$_3$)$_2$ | C$_2$H$_5$ | 0 | — | 164-168 |
| 64 | 4-methylphenyl | CH$_3$ | CF(CF$_3$)$_2$ | C$_2$H$_5$ | 0 | — | 213-214 |
| 65 | 3-methylphenyl | CH$_3$ | CF(CF$_3$)$_2$ | C$_2$H$_5$ | 0 | — | |
| 66 | 2-methylphenyl | CH$_3$ | CF(CF$_3$)$_2$ | C$_2$H$_5$ | 0 | — | 106-112 |
| 67 | phenyl | CH$_3$ | CF(CF$_3$)$_2$ | C$_2$H$_5$ | 0 | — | |
| 68 | 4-(trifluoromethoxy)phenyl | CH$_3$ | CF(CF$_3$)$_2$ | CH$_3$ | 0 | — | |
| 69 | 2,3-dichlorophenyl | CH$_3$ | CF(CF$_3$)$_2$ | CH$_3$ | 0 | — | |
| 70 | 2,5-dichlorophenyl | CH$_3$ | CF(CF$_3$)$_2$ | CH$_3$ | 0 | — | |
| 71 | 4-(trifluoromethyl)phenyl | CH$_3$ | CF(CF$_3$)$_2$ | CH$_3$ | 0 | — | |
| 72 | 2,6-difluorophenyl | CH$_3$ | CF(CF$_3$)$_2$ | CH$_3$ | 0 | — | 145-148 |
| 73 | 2,3-difluorophenyl | CH$_3$ | CF(CF$_3$)$_2$ | CH$_3$ | 0 | — | |
| 74 | 2,4-difluorophenyl | CH$_3$ | CF(CF$_3$)$_2$ | CH$_3$ | 0 | — | |
| 75 | 2-chlorophenyl | CH$_3$ | CF(CF$_3$)$_2$ | CH$_3$ | 0 | — | 141-145 |
| 76 | 3-chlorophenyl | CH$_3$ | CF(CF$_3$)$_2$ | CH$_3$ | 0 | — | |
| 77 | 4-chlorophenyl | CH$_3$ | CF(CF$_3$)$_2$ | CH$_3$ | 0 | — | 211-212 |
| 78 | 4-ethoxyphenyl | CH$_3$ | CF(CF$_3$)$_2$ | CH$_3$ | 0 | — | |
| 79 | 4-(trifluoromethylthio)phenyl | CH$_3$ | CF(CF$_3$)$_2$ | CH$_3$ | 0 | — | |
| 80 | 3-fluorophenyl | CH$_3$ | CF(CF$_3$)$_2$ | CH$_3$ | 0 | — | |
| 81 | 2-fluorophenyl | CH$_3$ | CF(CF$_3$)$_2$ | CH$_3$ | 0 | — | |
| 82 | 4-methylsulfinylphenyl | CH$_3$ | CF(CF$_3$)$_2$ | CH$_3$ | 0 | — | |
| 83 | 4-(trifluoromethylsulfinyl)phenyl | CH$_3$ | CF(CF$_3$)$_2$ | CH$_3$ | 0 | — | |
| 84 | 4-methylsulfonylphenyl | CH$_3$ | CF(CF$_3$)$_2$ | CH$_3$ | 0 | — | |
| 85 | 4-(trifluoromethylsulfonyl)phenyl | CH$_3$ | CF(CF$_3$)$_2$ | CH$_3$ | 0 | — | |
| 86 | 2-methylphenyl | CH$_3$ | CF(CF$_3$)$_2$ | CH$_3$ | 0 | — | |
| 87 | phenyl | CH$_3$ | C$_2$F$_5$ | CH$_3$ | 0 | — | |
| 88 | phenyl | CH$_3$ | CF(CF$_3$)$_2$ | CH$_3$ | 0 | — | 201-204 |
| 89 | 4-chlorophenyl | CH$_3$ | CF(CF$_3$)$_2$ | CH(CH$_3$)$_2$ | 0 | — | |
| 90 | 2-fluorophenyl | CH$_3$ | CF(CF$_3$)$_2$ | CH(CH$_3$)$_2$ | 0 | — | |
| 91 | 4-chlorophenyl | C$_2$H$_5$ | CF(CF$_3$)$_2$ | C$_2$H$_5$ | 0 | — | |
| 92 | 2,6-difluorophenyl | C$_2$H$_5$ | CF(CF$_3$)$_2$ | C$_2$H$_5$ | 0 | — | |
| 93 | 4-fluorophenyl | Cl | SCF$_3$ | Cl | 0 | — | |
| 94 | 3-fluorophenyl | Cl | SC$_2$F$_5$ | Cl | 0 | — | |
| 95 | 2-fluorophenyl | Cl | SC$_3$F7-n | Cl | 0 | — | |
| 96 | 2-chlorophenyl | Cl | S(O)CF$_3$ | Cl | 0 | — | |
| 97 | 3-chlorophenyl | Cl | S(O)C$_2$F$_5$ | Cl | 0 | — | |
| 98 | 4-chlorophenyl | Cl | S(O)C$_3$F7-n | Cl | 0 | — | |
| 99 | 2,6-difluorophenyl | Cl | SO$_2$CF$_3$ | Cl | 0 | — | |
| 100 | 2,3-difluorophenyl | Cl | SO$_2$S$_2$F$_5$ | Cl | 0 | — | |
| 101 | 2,4-difluorophenyl | Cl | SO$_2$C$_3$F7-n | Cl | 0 | — | |
| 102 | 4-chlorophenyl | CH$_3$ | SCF$_3$ | CH$_3$ | 0 | — | |
| 103 | 4-fluorophenyl | CH$_3$ | SC$_2$F$_5$ | CH$_3$ | 0 | — | |
| 104 | 2-fluorophenyl | CH$_3$ | SC$_3$F7-n | CH$_3$ | 0 | — | |
| 105 | 2,4-difluorophenyl | CH$_3$ | SO$_2$C$_3$F$_7$-n | CH$_3$ | 0 | — | |
| 106 | 4-methylthiophenyl | CH$_3$ | CF(CF$_3$)$_2$ | CH$_3$ | 0 | — | |
| 107 | 4-(trifluoromethyl)pyridin-3-yl | CH$_3$ | CF(CF$_3$)$_2$ | C$_2$H$_5$ | 1 | 2-F | |
| 108 | 4,6-difluoropyridin-3-yl | CH$_3$ | CF(CF$_3$)$_2$ | CH$_3$ | 1 | 2-F | |
| 109 | 6-chloropyridin-3-yl | CH$_3$ | CF(CF$_3$)$_2$ | CH$_3$ | 1 | 2-F | |
| 110 | 3-chloro-5-(trifluoromethyl)pyridin-2-yl | CH$_3$ | CF(CF$_3$)$_2$ | C$_2$H$_5$ | 1 | 2-F | |
| 111 | 2-bromophenyl | CH$_3$ | CF(CF$_3$)$_2$ | C$_2$H$_5$ | 1 | 2-F | |
| 112 | 3,4-dichlorophenyl | CH$_3$ | CF(CF$_3$)$_2$ | C$_2$H$_5$ | 1 | 2-F | |
| 113 | 2,4-dichlorophenyl | CH$_3$ | CF(CF$_3$)$_2$ | C$_2$H$_5$ | 1 | 2-F | |
| 114 | 2,6-dichlorophenyl | CH$_3$ | CF(CF$_3$)$_2$ | C$_2$H$_5$ | 1 | 2-F | |
| 115 | 2,3-dichlorophenyl | CH$_3$ | CF(CF$_3$)$_2$ | C$_2$H$_5$ | 1 | 2-F | |
| 116 | 2,5-dichlorophenyl | CH$_3$ | CF(CF$_3$)$_2$ | C$_2$H$_5$ | 1 | 2-F | |
| 117 | 3-(trifluoromethyl)phenyl | CH$_3$ | CF(CF$_3$)$_2$ | C$_2$H$_5$ | 1 | 2-F | |
| 118 | 2-(trifluoromethyl)phenyl | CH$_3$ | CF(CF$_3$)$_2$ | C$_2$H$_5$ | 1 | 2-F | |
| 119 | 2,4,6-trifluorophenyl | CH$_3$ | CF(CF$_3$)$_2$ | C$_2$H$_5$ | 1 | 2-F | |
| 120 | 2-nitrophenyl | CH$_3$ | CF(CF$_3$)$_2$ | C$_2$H$_5$ | 1 | 2-F | |
| 121 | 2,6-difluorophenyl | CH$_3$ | CF(CF$_3$)$_2$ | C$_2$H$_5$ | 1 | 2-F | |
| 122 | 2,3-difluorophenyl | CH$_3$ | CF(CF$_3$)$_2$ | C$_2$H$_5$ | 1 | 2-F | |

TABLE 1-continued

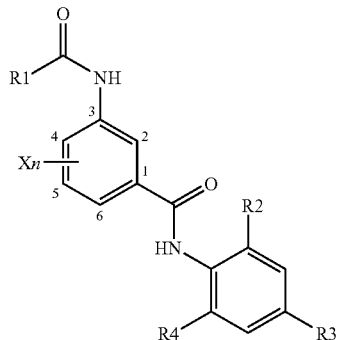

| No. | R1 | R2 | R3 | R4 | n | X | M.p. ° C. |
|---|---|---|---|---|---|---|---|
| 123 | 2,4-difluorophenyl | CH₃ | CF(CF₃)₂ | C₂H₅ | 1 | 2-F | |
| 124 | 2-chlorophenyl | CH₃ | CF(CF₃)₂ | C₂H₅ | 1 | 2-F | |
| 125 | 3-chlorophenyl | CH₃ | CF(CF₃)₂ | C₂H₅ | 1 | 2-F | |
| 126 | 4-chlorophenyl | CH₃ | CF(CF₃)₂ | C₂H₅ | 1 | 2-F | |
| 127 | 3-fluorophenyl | CH₃ | CF(CF₃)₂ | C₂H₅ | 1 | 2-F | |
| 128 | 2-fluorophenyl | CH₃ | CF(CF₃)₂ | C₂H₅ | 1 | 2-F | |
| 129 | 2,3-dichlorophenyl | CH₃ | CF(CF₃)₂ | CH₃ | 1 | 2-F | |
| 130 | 2,5-dichlorophenyl | CH₃ | CF(CF₃)₂ | CH₃ | 1 | 2-F | |
| 131 | 2,6-difluorophenyl | CH₃ | CF(CF₃)₂ | CH₃ | 1 | 2-F | |
| 132 | 2,3-difluorophenyl | CH₃ | CF(CF₃)₂ | CH₃ | 1 | 2-F | |
| 133 | 2,4-difluorophenyl | CH₃ | CF(CF₃)₂ | CH₃ | 1 | 2-F | |
| 134 | 2-chlorophenyl | CH₃ | CF(CF₃)₂ | CH₃ | 1 | 2-F | 193-194 |
| 135 | 3-chlorophenyl | CH₃ | CF(CF₃)₂ | CH₃ | 1 | 2-F | |
| 136 | 3-fluorophenyl | CH₃ | CF(CF₃)₂ | CH₃ | 1 | 2-F | |
| 137 | 2-fluorophenyl | CH₃ | CF(CF₃)₂ | CH₃ | 1 | 2-F | |
| 138 | 2-methylphenyl | CH₃ | CF(CF₃)₂ | CH₃ | 1 | 2-F | |
| 139 | 4-chlorophenyl | CH₃ | CF(CF₃)₂ | CH₃ | 1 | 2-F | 183-184 |
| 140 | 3,5-dichlorophenyl | CH₃ | CF(CF₃)₂ | C₂H₅ | 1 | 2-Cl | |
| 141 | 4-bromophenyl | CH₃ | CF(CF₃)₂ | C₂H₅ | 1 | 2-Cl | |
| 142 | 2-chlorophenyl | CH₃ | CF(CF₃)₂ | CH₃ | 1 | 2-Cl | >250 |
| 143 | 2-chlorophenyl | CH₃ | CF(CF₃)₂ | CH₃ | 1 | 2-CH₃ | >250 |
| 144 | 3-methoxy-5-(trifluoromethyl)thiophen-2-yl | CH₃ | CF(CF₃)₂ | C₂H₅ | 0 | — | 230-231 |
| 145 | 5-chloro-1-methyl-3-(trifluoromethyl)pyrazole | CH₃ | CF(CF₃)₂ | C₂H₅ | 0 | — | 101-106 |
| 146 | 4-bromo-1-ethyl-3-methylpyrazol-5-yl | CH₃ | CF(CF₃)₂ | C₂H₅ | 0 | — | 91-97 |
| 147 | 5-methylisoxazol-4-yl | CH₃ | CF(CF₃)₂ | C₂H₅ | 0 | — | 216-217 |
| 148 | isoxazol-5-yl | CH₃ | CF(CF₃)₂ | C₂H₅ | 0 | — | 91-99 |
| 149 | 2-chloropyridin-3-yl | CH₃ | CF(CF₃)₂ | CH₃ | 0 | — | 120-124 |
| 150 | 6-fluoropyridin-3-yl | CH₃ | CF(CF₃)₂ | C₂H₅ | 0 | — | |
| 151 | 6-fluoropyridin-3-yl | CH₃ | CF(CF₃)₂ | CH₃ | 0 | — | |
| 152 | 3-hydroxypyridin-2-yl | CH₃ | CF(CF₃)₂ | C₂H₅ | 0 | — | |
| 153 | 4-(trifluoromethyl)pyridin-2-yl | CH₃ | CF(CF₃)₂ | CH₃ | 0 | — | |
| 154 | 6-chloro-4-(trifluoromethyl)pyridin-3-yl | CH₃ | CF(CF₃)₂ | C₂H₅ | 0 | — | |

Synthesis Example 3

Raw Material/Intermediate

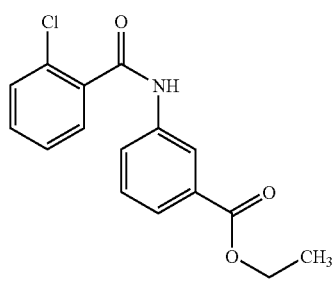

o-Chlorobenzoyl chloride (3.34 g) was added to THF (10 mL) solution containing ethyl m-aminobenzoate (3.00 g) and pyridine (2.16 g) in ice cooling condition. After the reaction mixture was stirred for 1 hour in ice cooling condition, it was poured to water and extraction was carried out with ethyl acetate. The organic layer was washed with water and dried by anhydrous magnesium sulfate. After the solvent was removed by distillation, the obtained coarse product was washed with a mixed solvent of hexane and tert-butyl methyl ether to obtain an aimed compound, 3-(2-chlorobenzoyl)aminobenzoic acid ethyl ether (5.00 g).

$^1$H NMR (300 MHz, CDCl₃) δ 8.18 (1H, br, s), 8.13 (1H, br, s), 8.09 (1H, d, J=8.1 Hz), 7.84 (1H, d, J=7.8 Hz), 7.74 (1H, d, J=7.8 Hz), 7.30-7.52 (4H, m), 4.34 (2H, q, J=7.2 Hz), 1.38 (3H, t, J=7.2 Hz).

Synthesis Example 4

Raw Material/intermediate

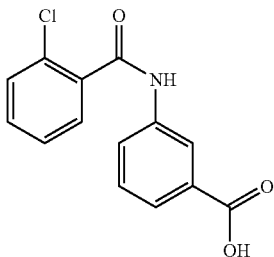

A mixture of 3-(2-chlorobenzoyl)aminobenzoic acid ethyl ether (4.00 g), potassium hydroxide (water 4.7 mL), and ethanol (20 mL) was stirred at room temperature for 4 hours. The reaction mixture was diluted with water and made acidic with 2N hydrochloric acid and the precipitated coarse product was washed with water and dried to obtain 3-(2-chlorobenzoyl)aminobenzoic acid (3.04 g).

$^1$H NMR (300 MHz, DMSO-d6) δ 13.0 (1H, br, s), 10.7 (1H, s), 8.40 (1H, s), 7.90 (1H, d, J=7.8 Hz), 7.70 (1H, d, J=7.8 Hz), 7.42-7.64 (5H, m).

Synthesis Example 5

Raw Material/intermediate

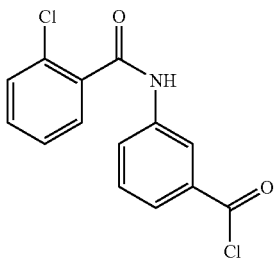

One drop of DMF was added to a 1,2-dichloroethane solution containing 3-(2-chlorobenzoyl)aminobenzoic acid (3.52 g) and further thionyl chloride (1.86 mL) was added and the mixture was heated and refluxed for 6 hours. After the solvent was removed by distillation, the coarse product, 3-(2-chlorobenzoyl)aminobenzoyl chloride, was used for the next step without refining treatment.

Biological Test Example 1

Test to Larvae of *Spodoptera litura*

Sample Solution Preparation
Solvent: dimethylformamide 3 part by weight
Emulsifier: polyoxyethylene alkyl phenyl ether 1 part by weight To prepare a proper active compound, the active compound 1 part by weight was mixed with the above-mentioned solvent containing the above-mentioned emulsifier and the mixture was diluted with water to a prescribed concentration.
Test Method
Leaves of batata were immersed in the sample solution diluted with water to a prescribed concentration and then the solution was dried out by air and the resulting leaves were put in a laboratory dish and 10 third stage larvae of *Spodoptera litura* were released and put in a greenhouse at a temperature 25° C. and the leaves of batata were added on second day and fourth day and the number of dead larvae was investigated after 7 days and the ratio of the dead larvae was calculated.

The results were the averages of two laboratory dishes for respective 1 group in this test.
Test Results
In the above-mentioned biological test example 1, as representative examples, the above-mentioned compounds 1, 3, 13, 24, 30, 32, 35, 36, 37, 38, 39, 40, 41, 42, 43, 44, 45, 46, 47, 48, 49, 51, 52, 53, 54, 55, 56, 57, 58, 59, 60, 61, 62, 63, 64, 66, 72, 77, 88, 134, 139 showed the breeding prevention and extermination effect of efficacious component concentration 20 ppm at 100% insecticidal ratio.

Biological Test Example 2

Test to Organic Phosphorus Agent- and Carbamate Agent-resistant *Myzus persicasypii*

Test Method
30 grown organic phosphorus agent- and carbamate agent-resistant *Myzus persicasypii* were inoculated in each vinyl pot with 6 cm diameter in which eggplant seeding was done and after 1 day from the inoculation, the above produced active compound diluted with water to have a prescribed concentration was sufficiently sprayed by a spray gun. After the spraying, the vinyl pots were left in a greenhouse at 28° C. and the insect extermination ratio was calculated after 7 days from spraying. The test was repeated two times.
Test Results
As representative examples, the above-mentioned compounds Nos. 1, 57, 58, 61, 63, and 139 showed breeding prevention and extermination effect of the efficacious component concentration 500 ppm at 100% insecticidal ratio.

Biological Test Example 3

Test to *Tetranychus urticae* (Spraying Test)

Test Method
50 to 100 adults of *Tetranychus urticae* were inoculated in leaves in two-leaf stage of kidney bean planted in pots with 6 cm diameter and after 1 day, the above produced active compound diluted with water to have a prescribed concentration was sufficiently sprayed by a spray gun. After the spraying, the pots were left in a greenhouse and the insect extermination ratio was calculated after 7 days from spraying.
Test Results
As representative examples, the above-mentioned compounds Nos. 1, 3, 13, 39, 43, 44, 45, 46, 47, 49, 54, 57, 58, 59, 61, 63, 64, 88, and 134 showed breeding prevention and extermination effect of the efficacious component concentration 500 ppm at 98% or higher insecticidal ratio.

Formulation Example 1

Granule

Water 25 parts was added to a mixture containing the compound of the invention (No. 1) 10 parts, bentonite (montmorillonite) 30 parts, talc 58 parts, and ligninsulfonic acid salt 2 part and the mixture was well kneaded and granulated with 10 to 40 meshes by an extruding granulator and dried at 40 to 50° C. to obtain granules.

Formulation Example 2

Granule 95 parts of clay mineral granules having particle diameter distribution of 0.2 to 2 mm were put in a rotary mixer and under rotating condition, the compound of the invention (No. 3) 5 parts together with a liquid diluent was sprayed and wetted evenly and dried at 40 to 50° C. to obtain granules.

Formulation Example 3

Emulsion

An emulsion was obtained by mixing the compound of the invention (No. 13) 30 part, xylene 55 part, polyoxyethylene alkylphenyl ether 8 part, and calcium alkylbenzenesulfonate 7 part.

Formulation Example 4

Hydrated Agent

A hydrated agent was obtained by mixing the compound of the invention (No. 24) 15 part, a mixture of white carbon (hydrated amorphous silicon oxide fine powder) and powdered clay (1:5) 80 part, sodium alkylbenzenesulfonate 2 part, and sodium alkylnaphthalenesulfonate-formalin condensate 3 part and crushing the mixture.

Formulation Example 5

Hydrated Granule

A hydrated granule was obtained by sufficiently mixing the compound of the invention (No. 30) 20 part, ligninsulfonic acid sodium salt 30 part, bentonite 15 part, fired kieselguhr powder 35 part, adding water, extruding the mixture with a 0.3 mm screen, and drying the extruded granules.

The invention claimed is:

1. A 3-acylaminobenzanilide of formula (I)

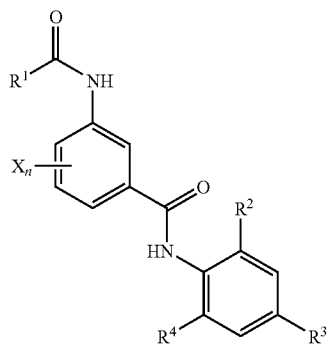

wherein
R$^1$ represents phenyl which may be substituted or a 5-member or 6-member heterocyclic ring group, which may be substituted, containing at least one hetero-atom selected from the group consisting of N, O, and S;
R$^2$ represents halogen, C$_{1-6}$ alkyl, or C$_{1-6}$ haloalkyl;
R$^3$ represents C$_{1-6}$ haloalkyl, C$_{1-6}$ haloalkoxy, C$_{1-6}$ haloalkylthio, C$_{1-6}$ haloalkylsulfinyl, or C$_{1-6}$ haloalkylsulfonyl;
R$^4$ represents halogen, C$_{1-6}$ alkyl, or C$_{1-6}$ haloalkyl;
X represents halogen, C$_{1-6}$ alkyl, or C$_{1-6}$ haloalkyl; and
represents 0 or 1.

2. The 3-acylaminobenzanilide according to claim 1, wherein
R$^1$ represents phenyl optionally substituted with at least one group selected from the group consisting of C$_{1-6}$ alkyl, C$_{1-6}$ alkoxy, C$_{1-6}$ alkylthio, C$_{1-6}$ alkylsulfinyl, C$_{1-6}$ alkylsulfonyl, C$_{1-6}$ haloalkyl, C$_{1-6}$ haloalkoxy, C$_{1-6}$ haloalkylthio, C$_{1-6}$ haloalkylsulfinyl, C$_{1-6}$ haloalkylsulfonyl, nitro, hydroxy, and halogen, or a 5-member or 6-member heterocyclic ring group containing at least one hetero-atom selected from the group consisting of N, O, and S and optionally substituted with at least one group selected from the group consisting of C$_{1-6}$ alkyl, C$_{1-6}$ alkoxy, C$_{1-6}$ alkylthio, C$_{1-6}$ alkylsulfinyl, C$_{1-6}$ alkylsulfonyl, C$_{1-6}$ haloalkyl, C$_{1-6}$ haloalkoxy, C$_{1-6}$ haloalkylthio, C$_{1-6}$ haloalkylsulfinyl, C$_{1-6}$ haloalkylsulfonyl, nitro, hydroxy, and halogen;
R$^2$ represents halogen, C$_{1-4}$ alkyl, or C$_{1-4}$ haloalkyl;
R$^3$ represents C$_{1-4}$ haloalkyl, C$_{1-4}$ haloalkoxy, C$_{1-4}$ haloalkylthio, C$_{1-4}$ haloalkylsulfinyl, or C$_{1-4}$ haloalkylsulfonyl;
R$^4$ represents halogen, C$_{1-4}$ alkyl, or C$_{1-4}$ haloalkyl;
X represents halogen, C$_{1-4}$ alkyl, or C$_{1-4}$ haloalkyl; and
n represents 0 or 1.

3. The 3-acylaminobenzanilide according to claim 1, wherein
R$^1$ represents phenyl optionally substituted with at least one group selected from the group consisting of C$_{1-4}$ alkyl, C$_{1-4}$ alkoxy, C$_{1-4}$ alkylthio, C$_{1-4}$ alkylsulfinyl, C$_{1-4}$ alkylsulfonyl, C$_{1-4}$ haloalkyl, C$_{1-4}$ haloalkoxy, C$_{1-4}$ haloalkylthio, C$_{1-4}$ haloalkylsulfinyl, C$_{1-4}$ haloalkylsulfonyl, nitro, hydroxy, and halogen; or pyridyl, pyrazolyl, thienyl, furyl, isoxazolyl, or thiadiazolyl optionally substituted with at least one group selected from the group consisting of C$_{1-4}$ alkyl, C$_{1-4}$ alkoxy, C$_{1-4}$ alkylthio, C$_{1-4}$ alkylsulfinyl, C$_{1-4}$ alkylsulfonyl, C$_{1-4}$ haloalkyl, C$_{1-4}$ haloalkoxy, C$_{1-4}$ haloalkylthio, C$_{1-4}$ haloalkylsulfinyl, C$_{1-4}$ haloalkylsulfonyl, nitro, hydroxy, and halogen;
R$^2$ represents fluoro, chloro, iodo, methyl, ethyl, propyl, butyl, trifluoromethyl, or pentafluoroethyl;
R$^3$ represents C$_{1-4}$ haloalkyl, C$_{1-4}$ haloalkoxy, C$_{1-4}$ haloalkylthio, C$_{1-4}$ haloalkylsulfinyl, or C$_{1-4}$ haloalkylsulfonyl;
R$^4$ represents fluoro, chloro, iodo, methyl, ethyl, n-propyl, i-propyl, n-butyl, i-butyl, t-butyl, trifluoromethyl or pentafluoroethyl;
X represents fluoro, chloro, or methyl; and
n represents 0 or 1.

4. A process for the preparation of the 3-acylaminobenzamide of formula (I) according to claim 1
(a):
comprising reacting a compound of formula (II)

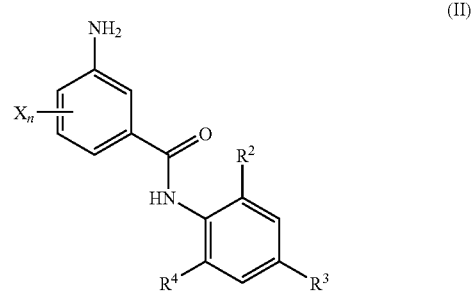

wherein R$^2$, R$^3$, R$^4$, X, and n are defined in claim 1, with a compound of formula (III)

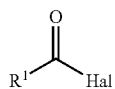
(III)

wherein R¹ is defined in claim 1 and Hal represents a halogen, in the presence of an inert solvent or (b):

reacting a compound of formula (IV)

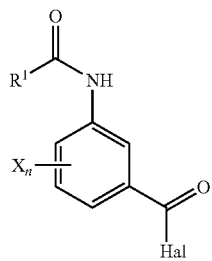
(IV)

wherein R¹, X and n are defined in claim 1 and Hal represents a halogen, with a compound of formula (V)

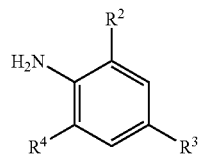
(V)

wherein $R^2$, $R^3$, and $R^4$ are defined in claim 1, in the presence of an inert solvent.

5. An insecticidal composition comprising at least one 3-acylaminobenzanilide according to claim 1.

6. A process for combating harmful insects comprising allowing the 3-acylaminobenzanilide according to claim 1 to act on harmful insects and/or their habitat and/or propagation material.

7. A process for the preparation of the insecticidal composition according to claim 5 comprising mixing the 3-Acylaminobenzanilide with extenders and/or surface active agents.

8. A method for treating seeds comprising applying the composition according to claim 5 to said seeds.

9. A method for treating transgenic plants comprising applying the composition according to claim 5 to said transgenic plants.

10. A method for treating seeds of transgenic plants comprising applying the composition according to claim 5 to said seeds of transgenic plants.

11. A method of controlling harmful insects comprising contacting said insects with a 3-acylaminobenzanilide according to claim 1.

12. The method according to claim 4 wherein the compound of formula (II) and the compound of formula III are reacted in the presence of a base and a phase transfer catalyst.

13. The method according to claim 4 wherein the compound of formula (IV) and the compound of formula (V) are reacted in the presence of a base and a phase transfer catalyst.

* * * * *